(12) United States Patent
Ingber

(10) Patent No.: US 10,082,452 B2
(45) Date of Patent: Sep. 25, 2018

(54) FILTER ARRANGEMENT AND METHOD FOR USING THE SAME

(71) Applicant: POCARED Diagnostics LTD., Rehovot (IL)

(72) Inventor: Gal Ingber, Oranit (IL)

(73) Assignee: POCARED Diagnostics LTD., Rehovot (IL)

( * ) Notice: Subject to any disclaimer, the term of this patent is extended or adjusted under 35 U.S.C. 154(b) by 588 days.

(21) Appl. No.: 14/172,491

(22) Filed: Feb. 4, 2014

(65) Prior Publication Data

US 2014/0246389 A1 Sep. 4, 2014

Related U.S. Application Data

(60) Provisional application No. 61/760,954, filed on Feb. 5, 2013, provisional application No. 61/789,027, filed on Mar. 15, 2013.

(51) Int. Cl.
  *G01N 1/40* (2006.01)
  *G01N 1/34* (2006.01)
  *B01L 3/00* (2006.01)

(52) U.S. Cl.
  CPC .......... *G01N 1/34* (2013.01); *B01L 3/502753* (2013.01); *G01N 1/4077* (2013.01); *B01L 2300/0681* (2013.01); *B01L 2300/0816* (2013.01); *B01L 2300/0887* (2013.01); *B01L 2400/049* (2013.01); *G01N 2001/4088* (2013.01)

(58) Field of Classification Search
  None
  See application file for complete search history.

(56) References Cited

U.S. PATENT DOCUMENTS

| | | | |
|---|---|---|---|
| 4,096,062 A | 6/1978 | Myréen et al. |
| 4,208,187 A | 6/1980 | Givner |
| 4,214,993 A | 7/1980 | Forsythe, Jr. et al. |
| 4,382,808 A | 5/1983 | Van Wormer, Jr. et al. |
| 4,540,490 A | 9/1985 | Shibata et al. |
| 4,544,386 A | 10/1985 | Trayford, III et al. |

(Continued)

FOREIGN PATENT DOCUMENTS

| | | |
|---|---|---|
| CN | 1713951 A | 12/2005 |
| CN | 102596373 A | 7/2012 |

(Continued)

*Primary Examiner* — Patrick James Orme
(74) *Attorney, Agent, or Firm* — The Webb Law Firm

(57) ABSTRACT

A filter arrangement with a top element and a bottom element and a filter element therebetween captures oversized particles on the upper surface of the filter element and tangentially rinses these particles using an elution fluid to provide a concentration of particles in a relatively low volume of fluid for further analysis. In an intermediate step, the particles captured by the filter may be rinsed with a rinsing fluid such as water to pass additional undersized particles through the filter, thereby providing a purer sample. To improve efficiency, check valves may be used for passageways with one-way flow. Additionally, a configuration of three-way stopcocks may also be utilized. Finally, a sandwich arrangement is possible, wherein a single bottom element is sandwiched between two opposing top elements.

10 Claims, 18 Drawing Sheets

(56) References Cited

U.S. PATENT DOCUMENTS

| | | | |
|---|---|---|---|
| 4,649,760 A | 3/1987 | Wedding | |
| 4,973,450 A | 11/1990 | Schlueter | |
| 4,999,164 A | 3/1991 | Puchinger et al. | |
| 5,151,244 A | 9/1992 | Law et al. | |
| 5,243,864 A | 9/1993 | Dunmyre et al. | |
| 5,251,496 A | 10/1993 | Platek | |
| 5,783,938 A | 7/1998 | Munson et al. | |
| 6,117,394 A | 9/2000 | Smith | |
| 6,171,656 B1 | 1/2001 | Settles | |
| 6,269,703 B1 | 8/2001 | Bowers | |
| 6,382,036 B1 | 5/2002 | Woodmansee | |
| 6,444,001 B1 | 9/2002 | Sheffield | |
| 6,458,267 B2 | 10/2002 | Kaendler | |
| 6,482,362 B1 | 11/2002 | Smith | |
| 6,484,594 B1 | 11/2002 | Saaski et al. | |
| 6,523,393 B1 | 2/2003 | Linker et al. | |
| 6,532,835 B1 | 3/2003 | Saaski et al. | |
| 6,604,406 B1 | 8/2003 | Linker et al. | |
| 6,641,545 B1 | 11/2003 | Colin et al. | |
| 6,641,733 B2 | 11/2003 | Zha et al. | |
| 6,672,135 B2 | 1/2004 | Adiletta | |
| 6,692,702 B1 | 2/2004 | Burshteyn et al. | |
| 6,692,968 B2 | 2/2004 | Burshteyn et al. | |
| 6,723,289 B2 | 4/2004 | Iheme et al. | |
| 6,857,436 B2 | 2/2005 | Labib et al. | |
| 7,100,461 B2 | 9/2006 | Bradley et al. | |
| 7,155,988 B2 | 1/2007 | Cole et al. | |
| 7,318,911 B2 | 1/2008 | Smith | |
| 7,334,453 B2 | 2/2008 | Trakumas et al. | |
| 7,350,536 B2 | 4/2008 | Evans | |
| 7,695,627 B2 | 4/2010 | Bosch et al. | |
| 7,880,874 B2 | 2/2011 | Pochy | |
| 8,052,778 B2 | 11/2011 | McFarland et al. | |
| 8,110,112 B2 | 2/2012 | Alburty et al. | |
| 8,518,636 B2 | 8/2013 | Bosch et al. | |
| 8,584,535 B2 | 11/2013 | Page et al. | |
| 8,584,536 B2 | 11/2013 | Page et al. | |
| 9,174,212 B2 | 11/2015 | Huang | |
| 2002/0030015 A1 | 3/2002 | Stipanovic et al. | |
| 2008/0023381 A1 | 1/2008 | Jackson et al. | |
| 2008/0028873 A1 | 2/2008 | Yao et al. | |
| 2009/0101575 A1* | 4/2009 | Alburty | G01N 1/4077 210/636 |
| 2010/0051527 A1 | 3/2010 | Frandsen | |
| 2010/0313685 A1 | 12/2010 | Page et al. | |
| 2010/0313686 A1 | 12/2010 | Page et al. | |
| 2011/0061474 A1 | 3/2011 | Page et al. | |
| 2011/0067505 A1 | 3/2011 | Page et al. | |
| 2011/0108483 A1 | 5/2011 | Kaas | |
| 2011/0197685 A1 | 8/2011 | Alburty et al. | |
| 2015/0108056 A1 | 4/2015 | Charest et al. | |

FOREIGN PATENT DOCUMENTS

| | | |
|---|---|---|
| JP | 2000176258 A | 6/2000 |
| JP | 2005529746 A | 10/2005 |
| JP | 2012239991 A | 12/2012 |
| WO | 2011079217 A1 | 6/2011 |

* cited by examiner

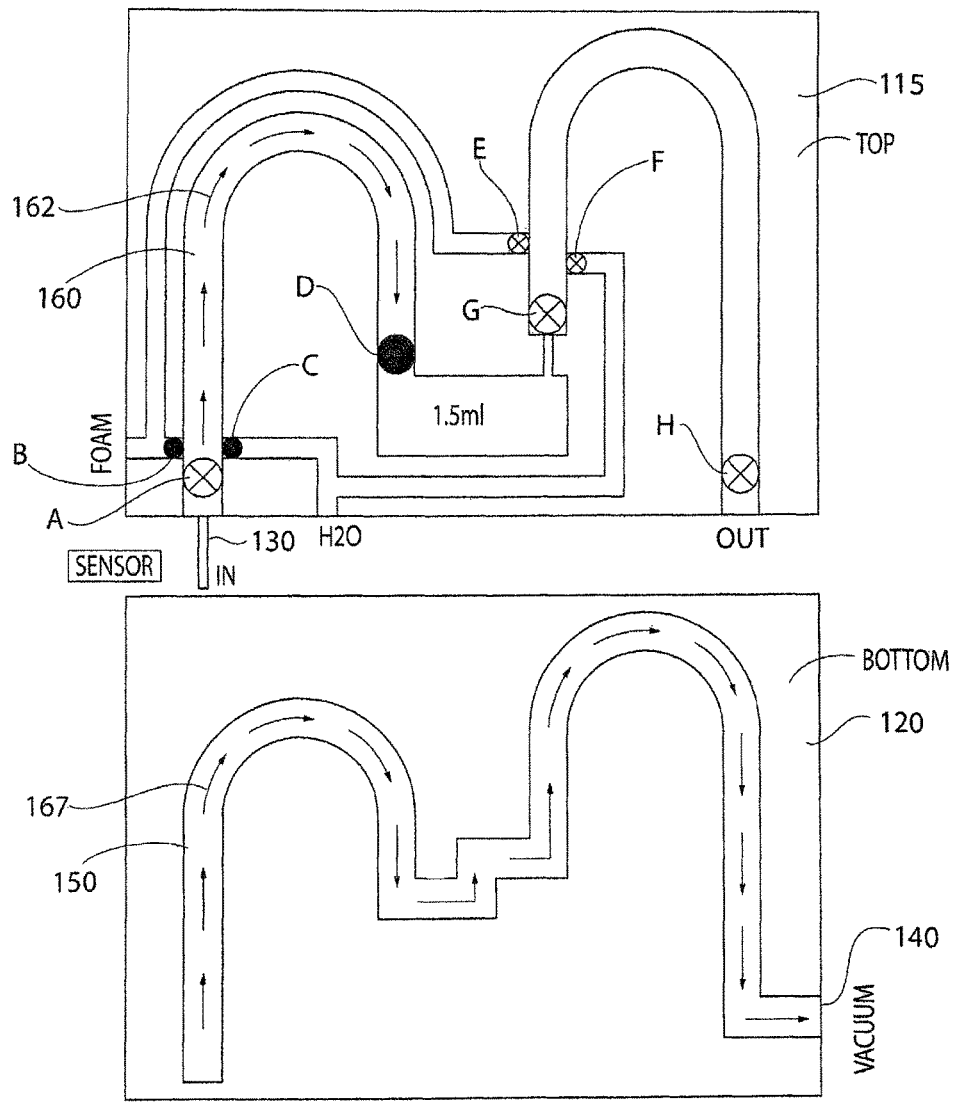
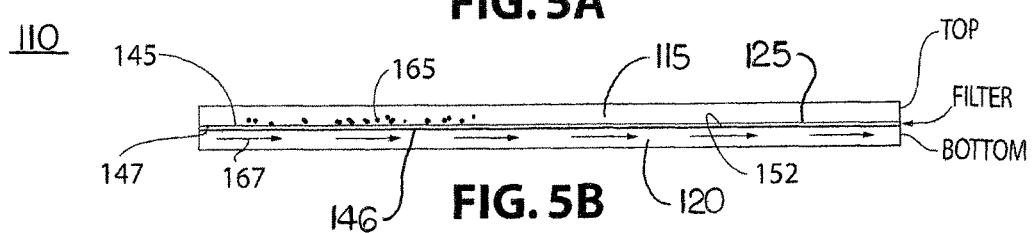
FIG. 5A
FIG. 5B

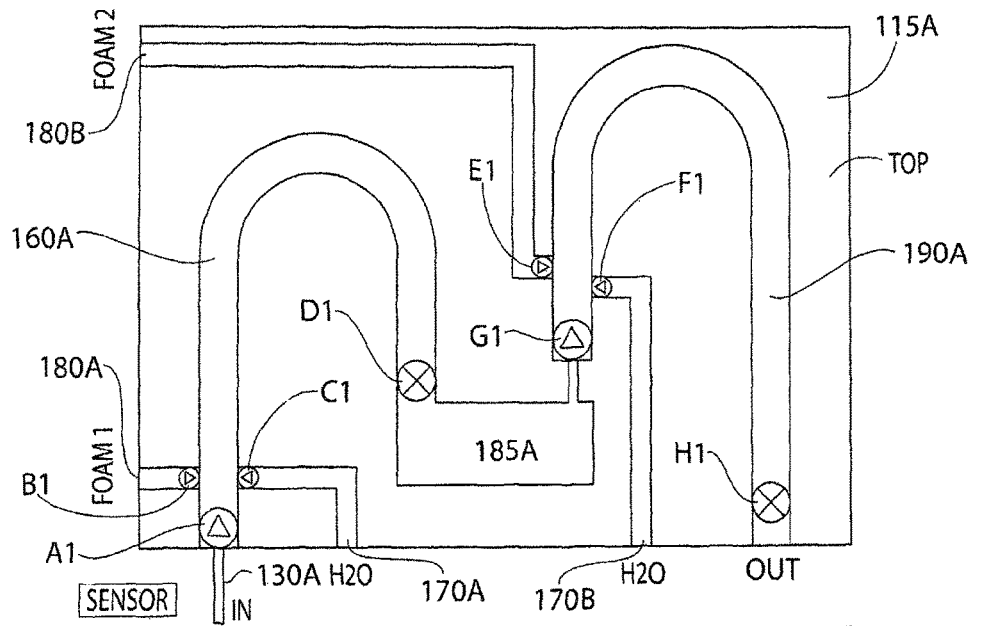
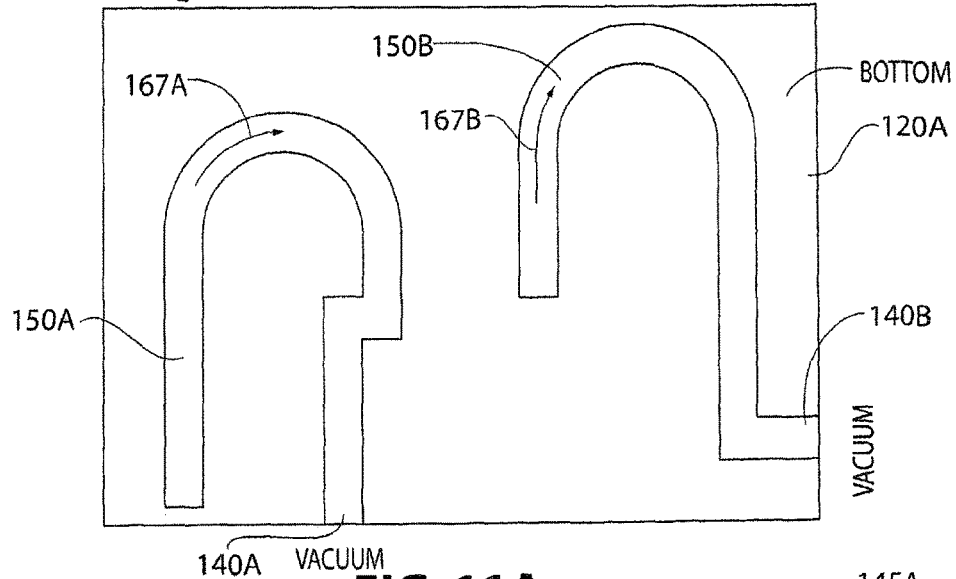
FIG. 11A
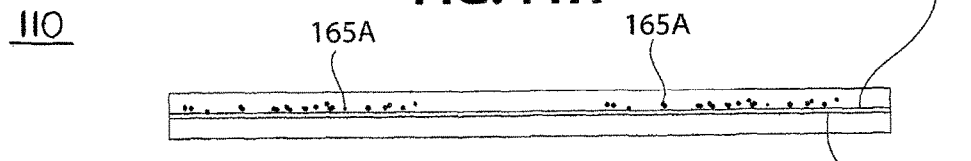
FIG. 11B

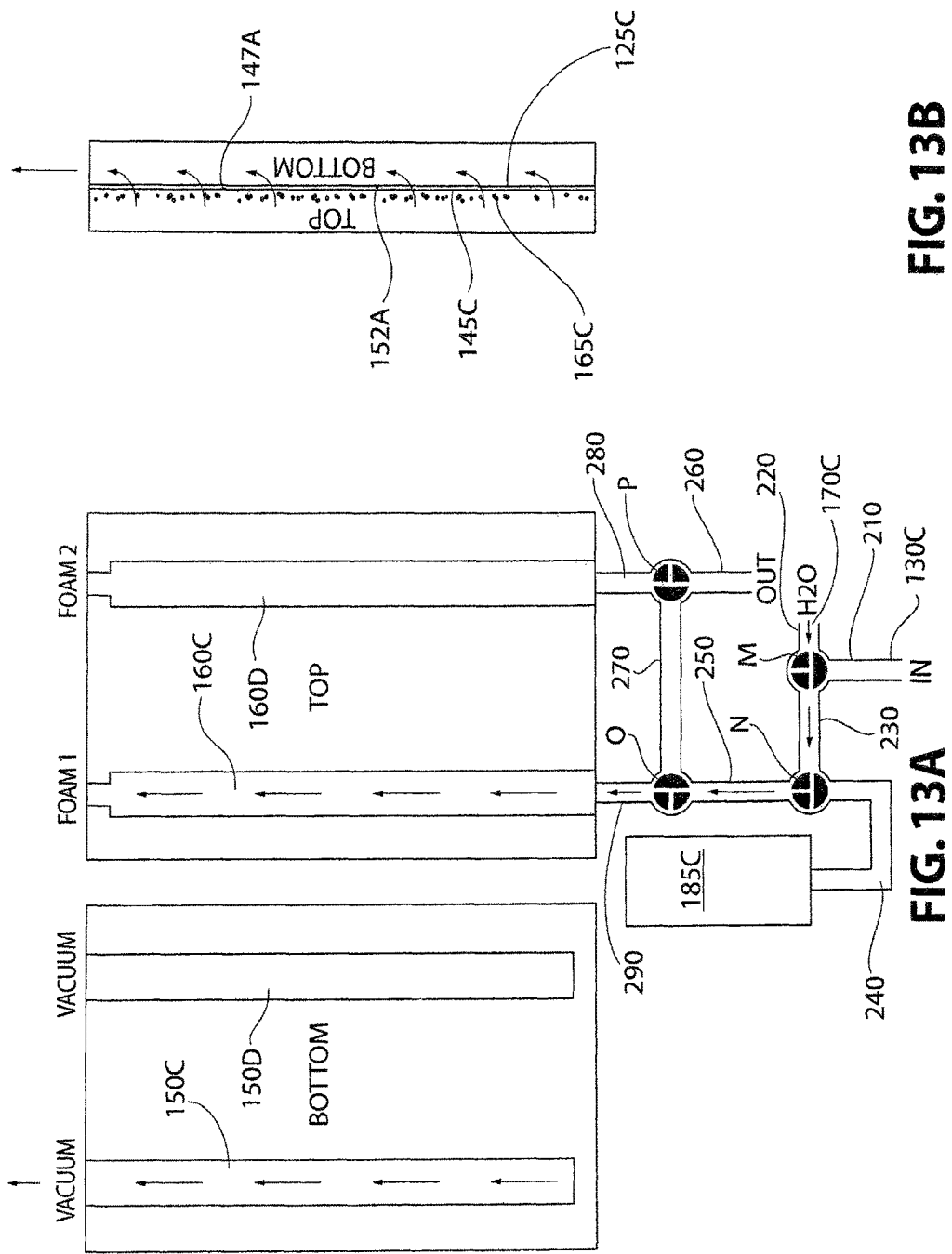

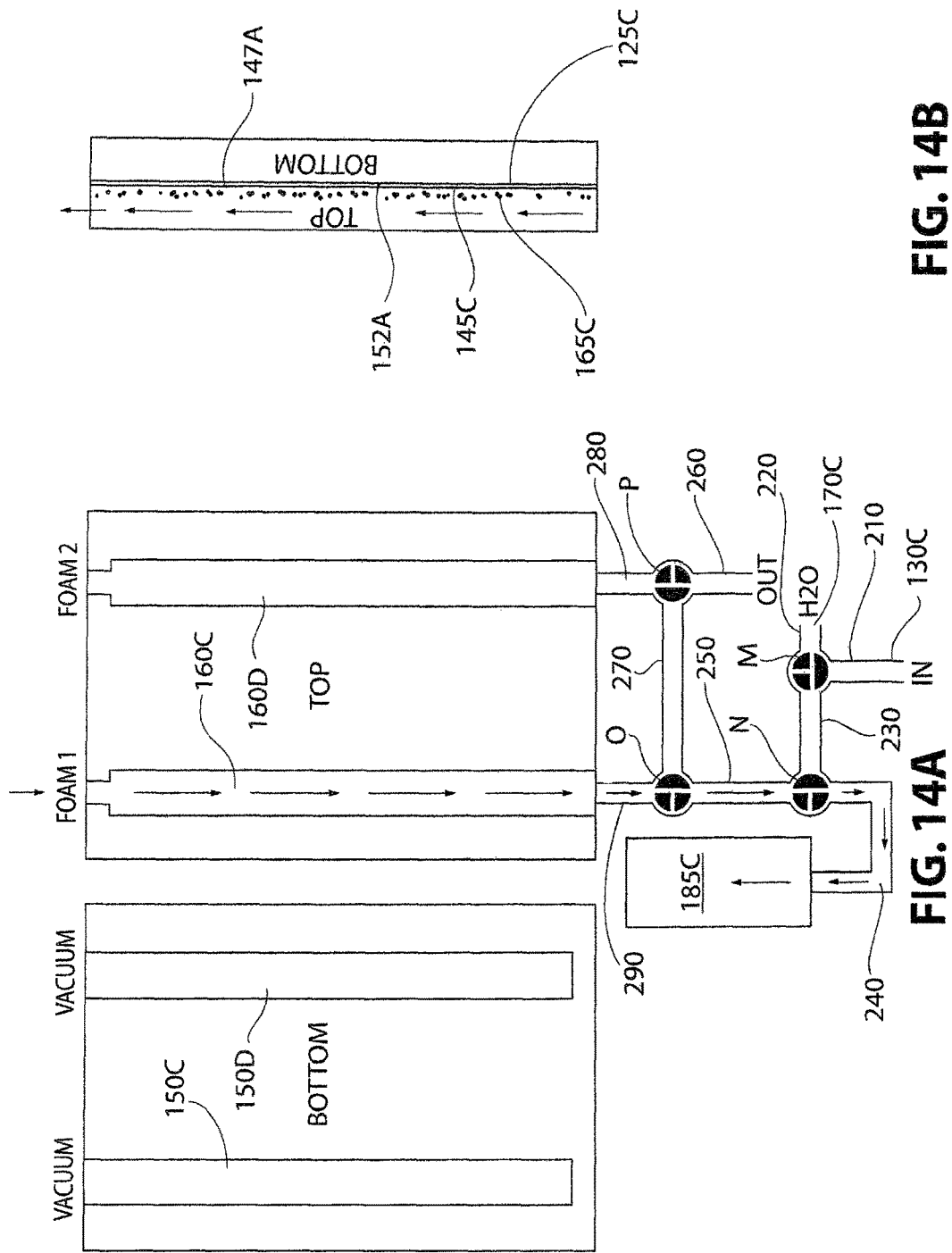

FILTER ARRANGEMENT AND METHOD FOR USING THE SAME

CROSS-REFERENCE TO RELATED APPLICATIONS

This application claims the benefit of U.S. Provisional Application Nos. 61/760,954, filed Feb. 5, 2013 and 61/789,027 filed Mar. 15, 2013. The disclosure of each of these documents is hereby incorporated in its entirety by reference.

BACKGROUND OF THE INVENTION

Field of the Invention

Mechanical particle filters are used to extract particles for analysis from a fluid/particle mixture. However, now the particles are retained by the filter. The most common technique for removing particles from a filter for analysis is to introduce additional fluid, such as by using a backwashing process. However, ideally, the particles should be contained in the smallest amount of fluid possible while maintaining high retention ratio for ease of analysis. This is especially true when the particles are bacteria. Therefore, while backwashing a filter does remove the particles from the filter, the efficiency of the process is low and the quantity of fluid required may produce a secondary fluid/particle mixture with excessive fluid.

Furthermore, when using hydrophilic membrane with small pore size and when suction is provided on the downstream side of the filter to draw fluid and undersized particles, often times, the membrane will become a barrier to air after it was wetted.

A design and method are needed, whereby the particles of interest may be filtered and contained within a small volume of fluid and, furthermore, whereby the filter may be constructed such that, even after the fluid passes, the membranes of the filter will allow more suction using vacuum.

BRIEF DESCRIPTION OF THE DRAWINGS

FIGS. 5A-10A are schematic views of the top half and bottom half of one embodiment of the filter arrangement in accordance with the subject invention illustrating different configurations for the filtering process;

FIGS. 5B-10B are schematics of the filter arrangement in the assembled state showing different configurations for the filtering process;

FIG. 11A is a schematic view of the top half and bottom half of one embodiment of the filter arrangement utilizing check valves and modified channels to provide dual inlets for the elution and water and dual outlets for the vacuum;

FIG. 11B is a schematic view of the filter arrangement in FIG. 11A in the assembled state;

FIGS. 12A-17A are schematic views of the top half and bottom half of another embodiment of the filter arrangement illustrating different configurations for the filtering process and, furthermore, utilizing stopcock valves to create different fluid paths;

FIGS. 12B-17B are schematic views of the filter arrangement of the embodiment illustrated in FIGS. 12A-17A in the assembled state showing different configurations for the filtering process;

DESCRIPTION OF THE INVENTION

Figure 1:
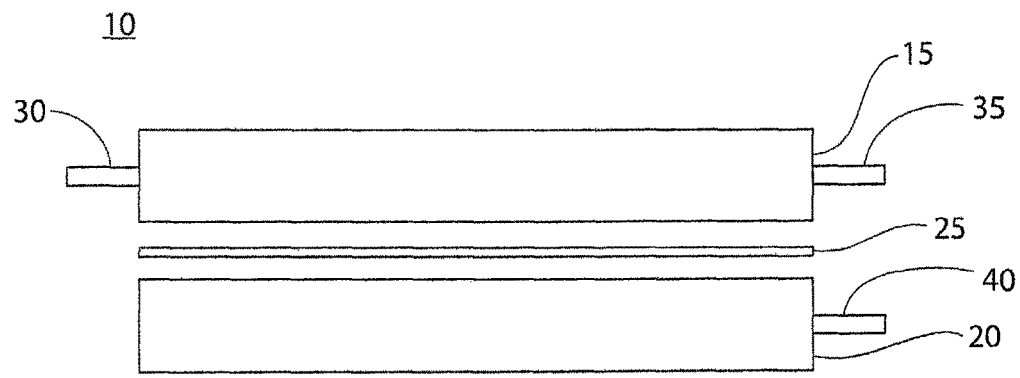
FIG. 1 is an exploded view of a simplified schematic showing a prior art filter arrangement.

For purposes of the description hereinafter, the terms "end", "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 2:
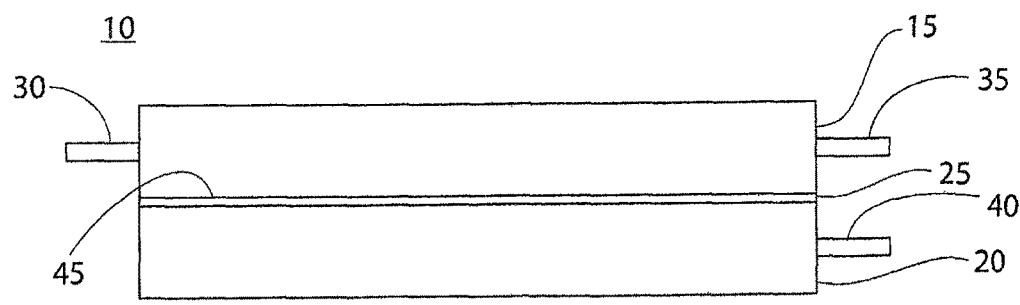
FIG. 2 is an assembled view of a schematic of the filter arrangement in FIG. 1.

FIG. 1 illustrates a prior art filter arrangement 10 having a top element 15, a bottom element 20, and a filter element 25 therebetween. FIG. 1 is an exploded schematic view, while FIG. 2 is an assembled schematic view of the same parts but with the top element 15 and the bottom element 20 drawn together to compress the filter element 25 therebetween. As an overview, directing attention to FIG. 2, a fluid/particle mixture is introduced through inlet/outlet 30 into channels (not shown) extending through the top element 15. Inlet 35 is closed and a suction outlet 40 provides a vacuum drawing the fluid/particle mixture through the filter element 25, such that oversized particles remain on the upper surface 45 of the filter element 25. Thereafter, the inlet 35 is open and the suction outlet 40 is closed. An elution fluid is then introduced into the inlet 35 to tangentially rinse the upper surface 45 of the filter element 25. This provides a reduced volume fluid/particle mixture that exits the inlet/outlet 30. As an intermediate step, it is possible to close the inlet 35 and to introduce a water/rinse into the inlet/outlet 30, while suction outlet 40 is open, to wash over the particles after the initial filtering step to further filter any remaining particles that were not previously washed through the filter. This water/rinse and undersized particle solution are removed through the suction outlet 40 and discarded. As a result, the oversized particles that were deposited upon the upper surface 45 of the filter element 25 are isolated and collected using a reduced volume elution fluid.

Figure 3:
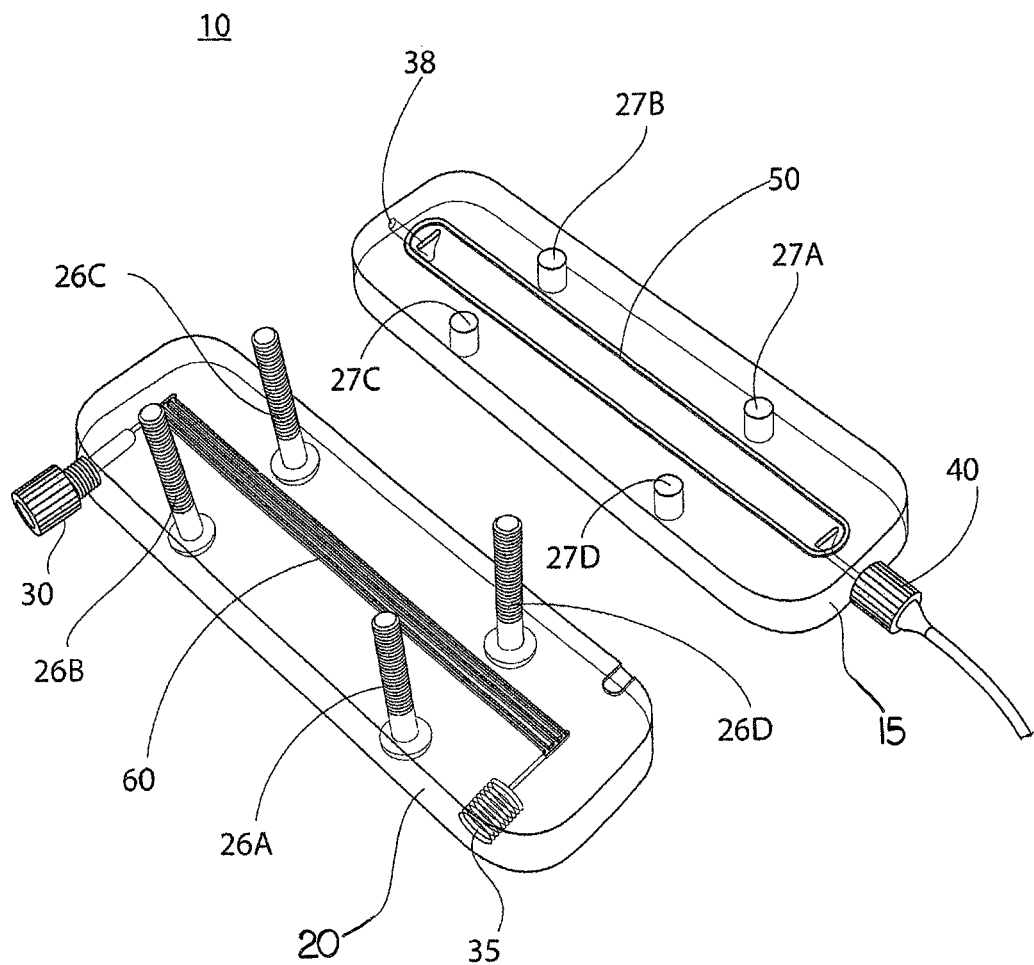
FIG. 3 is a sketch illustrating a perspective arrangement of a prior art the filter arrangement disassembled and without the filter element.
Figure 4:
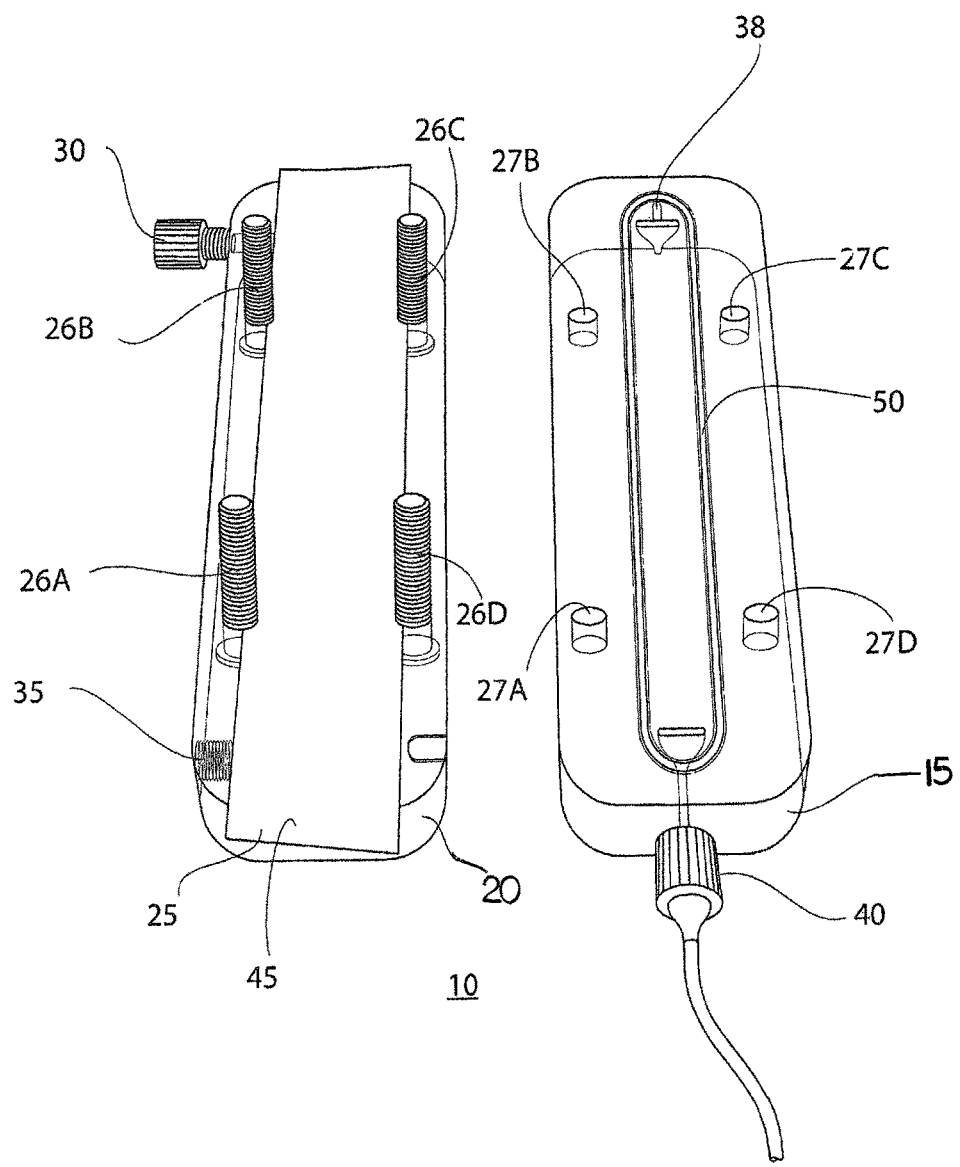
FIG. 4 is a sketch of the embodiment of the prior art filter arrangement of FIGS. 5A-10A illustrated in FIG. 9 but with a filter element placed in position.

FIGS. 3 and 4 illustrate a prior art embodiment of the filter arrangement 10 having a top element 15 and a bottom element 20 with a filter element 25 (FIG. 4) therebetween. Each of these figures is illustrated with a filter arrangement 10 in a disassembled state. However, it can be appreciated that the four bolts 26a, 26b, 26c, 26d may be secured within the bores 27a, 27b, 27c, 27d, respectively, with the filter element 25 therebetween to assemble the filter arrangement 10. The filter arrangement 10 illustrated in FIGS. 3 and 4, is a single-stage filter and the suction outlet 35 provides suction to the bottom channel 60. The top element 15 has an inlet/outlet 40 and an inlet 38, on the opposite side of inlet/outlet 40, with a channel 50 therebetween. The filter element 25 is positioned between the top element 15 and the bottom element 20. In operation, suction is provided at the suction outlet 35 such that there is a vacuum created in the bottom channel 60. The fluid/particle mixture is introduced through the inlet/outlet 40 of the top element 15 where it travels over the filter element 25 and oversized particles are retained on the upper surface 45 of the filter element 25. The fluid and undersized particles travel through the filter element 25 into the bottom channel 60 and are removed through the suction outlet 35. The oversized particles remain on the upper surface 45 of the filter element 25. Thereafter, suction is discontinued and elution fluid, under pressure, is introduced through the inlet 38 and into the channel 50 where it traverses the upper surface 45 and flushes the oversized particles into the outlet 40 where they are retained in a collector (not shown) for further analysis. The arrangement illustrated in FIGS. 3 and 4 does not include the intermediate step of rinsing the particles retained on the filter element 25 with water.

As known in the prior art, the elution fluid may be effervescent and contain a foaming agent identified by the trademark TWEEN® owned by Croda Americas LLC. The subject filtering arrangement is most effective when the particles are bacteria. The filter element is preferably a polycarbonate-type filter which is a surface filter and may have pores with openings approximately 0.4 microns wide.

For purposes or discussion, similar elements in different embodiments will be identified with similar numbers but with increments of 100, such as 10, 110, 210.

During the discussion of FIGS. 5A-10A, it should be appreciated that the surfaces illustrated for the top element 115 and the bottom element 120 may be transparent and the top element 115 will be placed over the bottom element 120, such that the channels in each of these elements 115, 120 are generally aligned with one another. Therefore, for purposes of discussion, the top element 115 is transparent and the channels illustrated therein will be on the underside 147 of the top element 115, while the bottom channel 150 illustrated in the bottom element 120 is on the upper side 152 of the bottom element 120. The filter element 125 is not illustrated in FIGS. 5A-10A but is located between the top element 115 and the bottom element 120 as shown in FIGS. 5B-10B. As further illustrated in FIGS. 5B-10B, the filter element 125 has an upper surface 145 that is contiguous with the underside 147 of the top element 115 and the filter element 125 has a lower surface 146 that is contiguous with the upper side 152 of the bottom element 120.

Valves A-H are illustrated in the top element 115. Depending upon the configuration of the filter arrangement 110, one or more of these valves will be open and others will be closed. Such closing will be illustrated by darkening the valve symbol.

For the initial configuration, directing attention to FIGS. 5A and 5B, the fluid/particle mixture is introduced through the inlet 130 and travels through the first-stage channel 160 as indicated by arrow 162. Valve A is open while valves B, C, and D are closed. In this configuration, a vacuum will be activated such that the suction outlet 140 draws a vacuum through the entire bottom channel 150. As a result, the fluid/particle mixture is urged against the upper surface 145 of the filter element 125 (FIG. 5B), thereby retaining oversized particles 165 on the upper surface 145 of the filter element 125. Undersized particles, along with fluid, are drawn through the filter element 125 and evacuated along the bottom channel 150 through the suction outlet 140, as indicated by arrows 167. At this point, oversized particles 165 and other miscellaneous particles have been deposited upon the upper surface 145 of the filter element 125. It should be noted that for the arrangement illustrated in FIGS. 5A and 5B, no more than one-half of the filter element 125 has been utilized.

To improve the integrity of the filtering process, the Inventors have learned that additional undersized particles will be washed through the filter element 125 simply by providing a fluid rinse, such as a water rinse, over the particles 165.

Figure 6A:
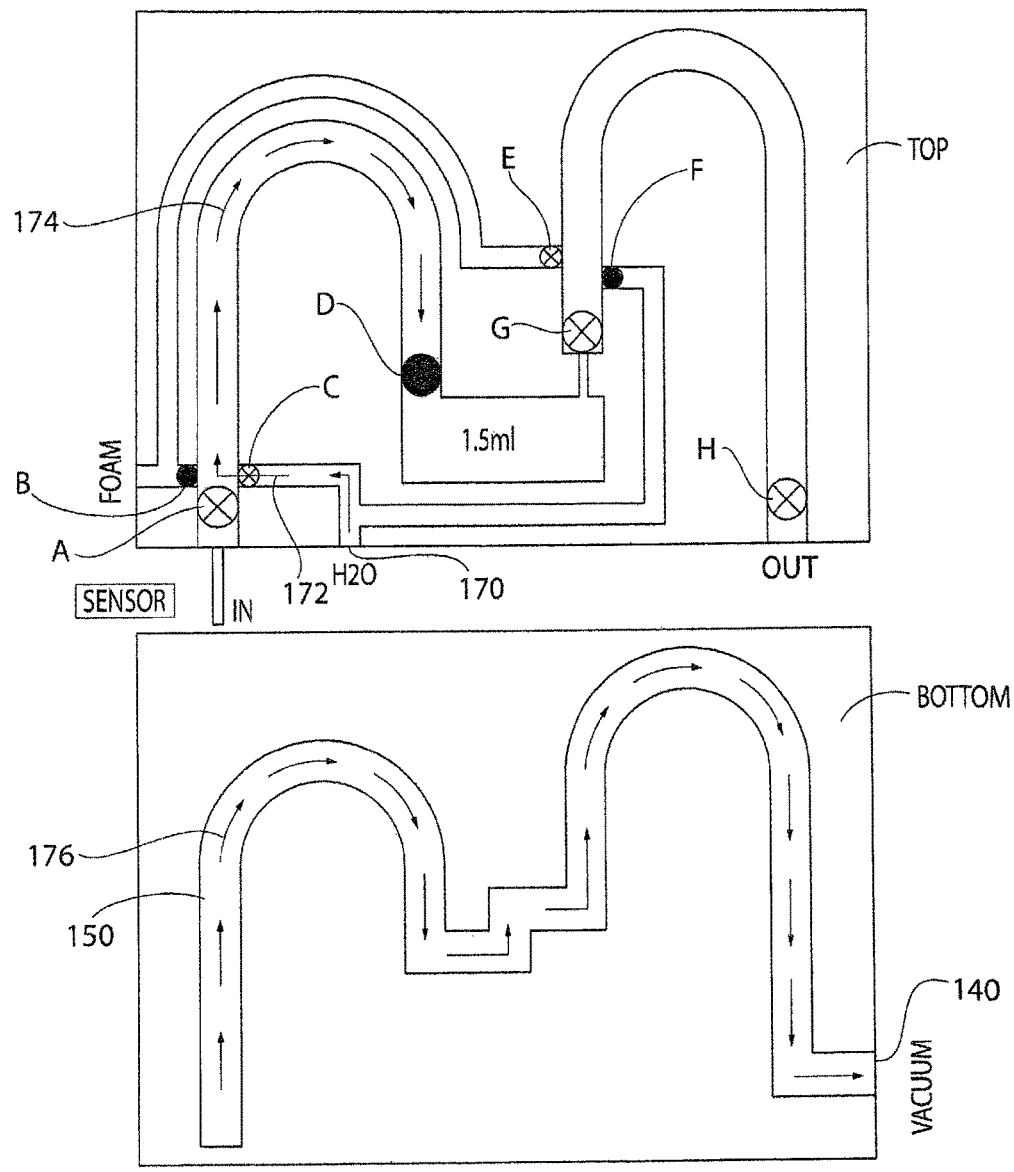
Figure 6B:
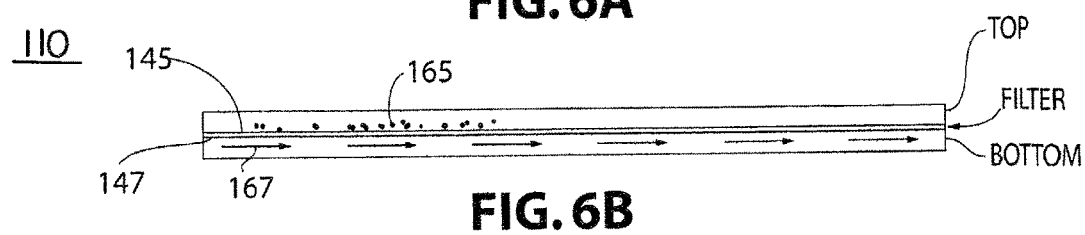

Directing attention to FIGS. 6A and 6B, valves A, B, D, and F are closed and water is introduced through water inlet 170 along the water channel 172, as illustrated by arrows 174. Just as with the original fluid/particle mixture, the suction outlet 140 provides a vacuum to the bottom channel 150 such that the water is drawn through the filter element 125 into the bottom channel 150 and follows arrows 176 where it is discharged at the suction outlet 140. This water rinse removes additional undersized particles that may have been retained during the initial filter step.

Figure 7A:
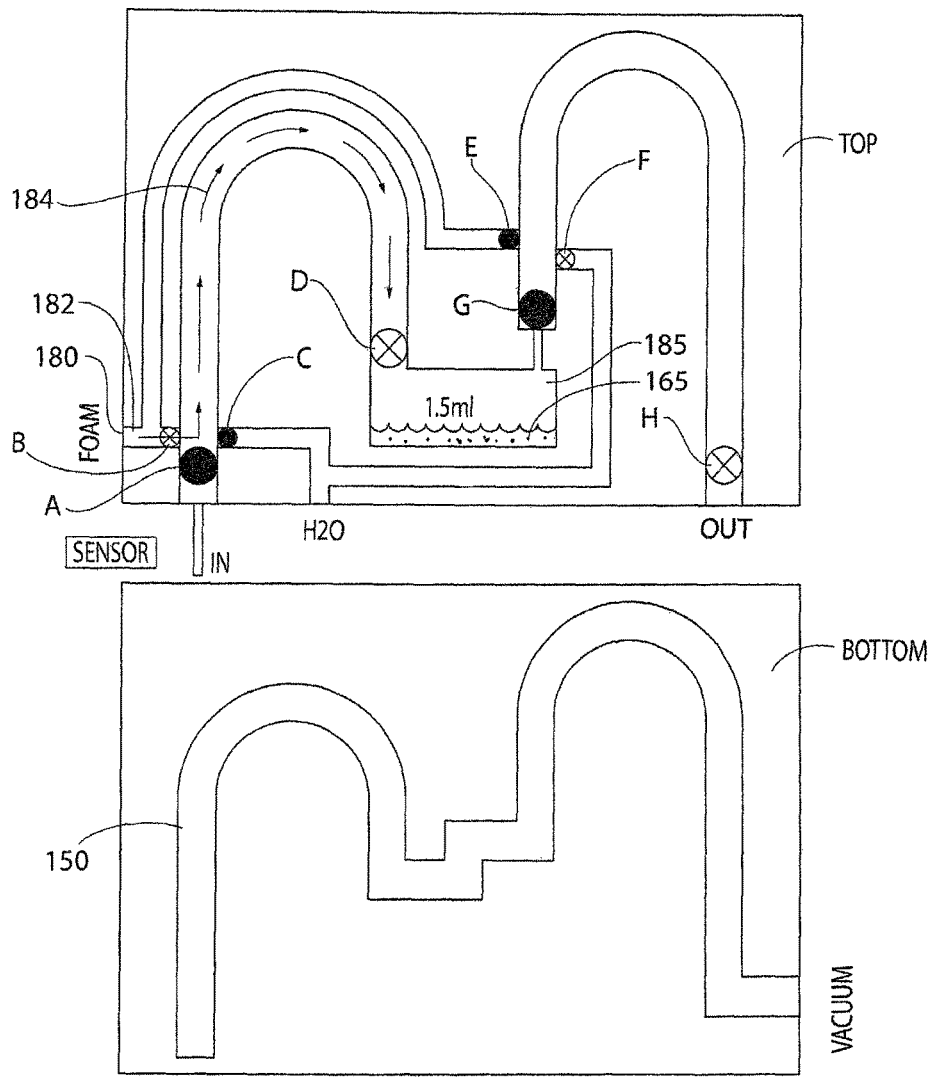
Figure 7B:
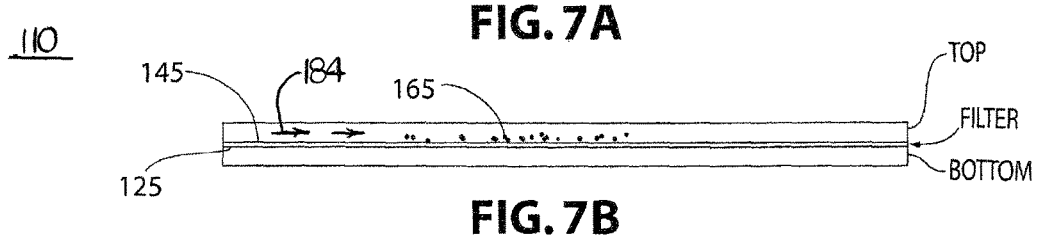

Direction attention to FIGS. 7A and 7B, valves A, C, E, and G are now closed and the elution fluid, which will also be referred to as foam, is introduced under pressure at the foam inlet 180 where it travels through the foam channel 182 in a path defined by arrows 184 to a collector 185, which now contains a reduced volume fluid/particle mixture, wherein the fluid is the elution fluid. It should be noted that the vacuum is off, such that the bottom channel 150 is inactive and the flow of the elution fluid travels across the upper surface 145 of the filter element 125 to deposit the fluid/particle mixture within the collector 185. This process of passing the fluid across the upper surface 145 of the filter element 125 is known as tangentially rinsing the upper surface 152 and dislodges the particles on the upper surface 145 to mechanically scrape the upper surface 145 and move the particles 165 into the collector 185. By doing so, the relatively large volume of fluid associated with the initial fluid/particle mixture has been significantly reduced.

What has been described so far is a single-stage filtering process that provides a significant reduction in the volume of fluid associated with filtered particles to improve the ease of subsequent examination of the particles. Only a portion of the filter element 125, which extends essentially across the width of the bottom element 120, has been utilized.

The Inventors have realized that it is possible to provide a dual-stage filter with relative ease to further reduce the volume of fluid in the fluid/particle mixture or to further remove undesired small particles.

Figure 8A:
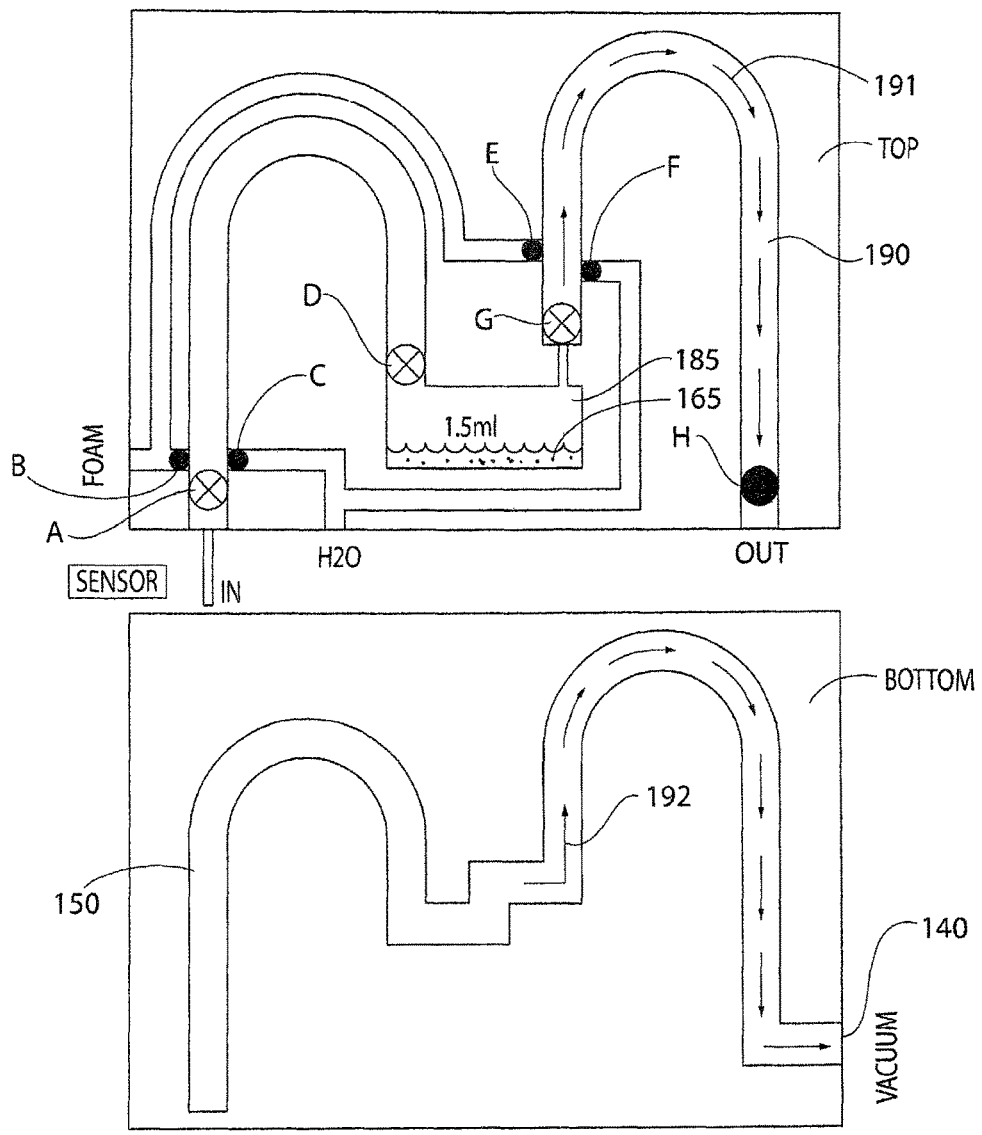
Figure 8B:
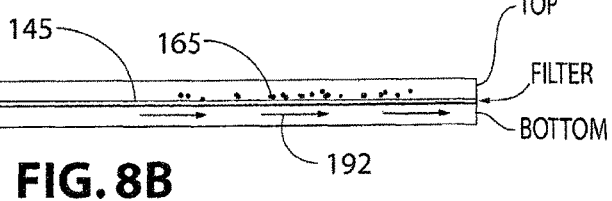

Directing attention to FIGS. 8A and 8B, with the refined fluid particle sample in the collector 185, valves B, C, E, F, and H are closed and suction is introduced to the bottom channel 150 such that fluid from the collector 185 is drawn into the second-stage channel 190 along arrows 191, where the undersized particles and the fluid are drawn through the filter element 125 into the bottom channel 150 and discharged through the suction outlet 140 along arrows 192. Additionally, valves A and D are open so that air can come in to permit fluid to be pulled out of reservoir 185. Once again, particles 165 are deposited upon the upper surface 145 of the filter element 125 but now the elution fluid and undersized particles are passed through the filter element 125 into the bottom channel 150 and out the suction outlet 140.

Figure 9A:
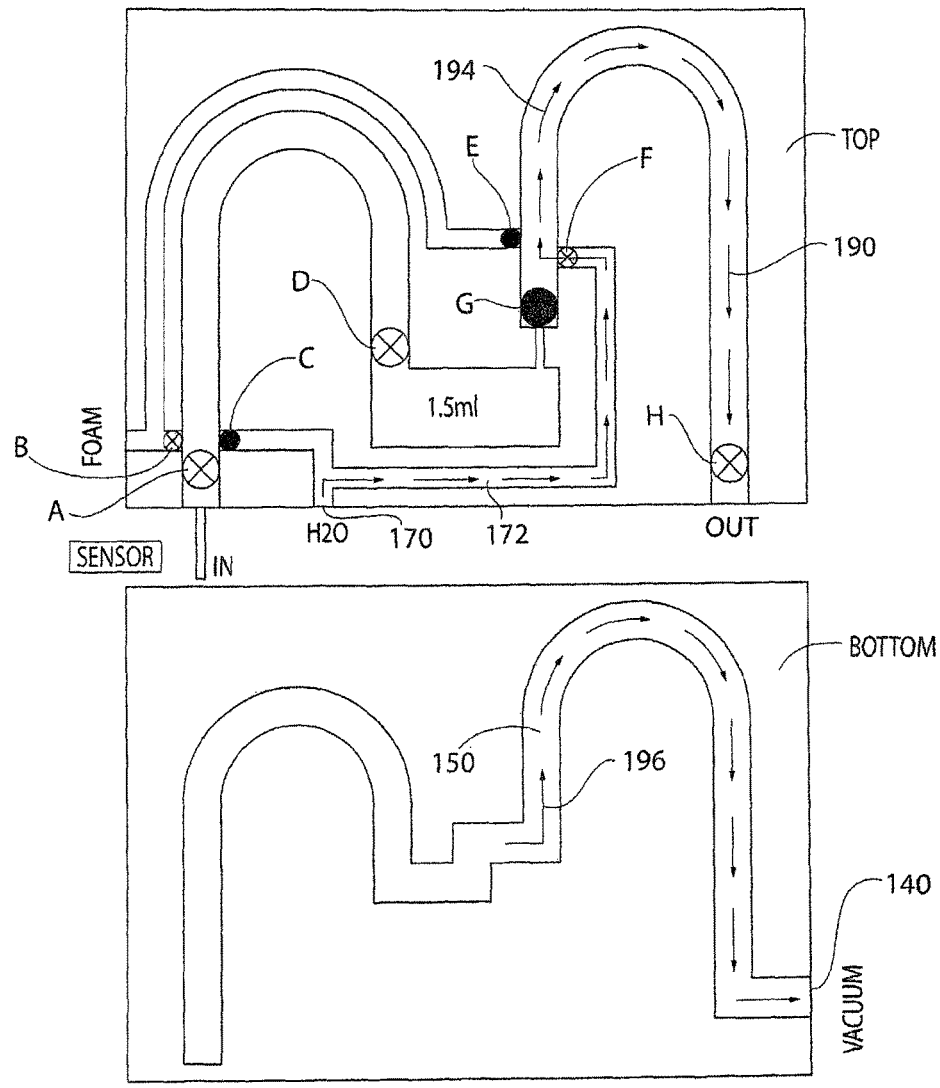
Figure 9B:
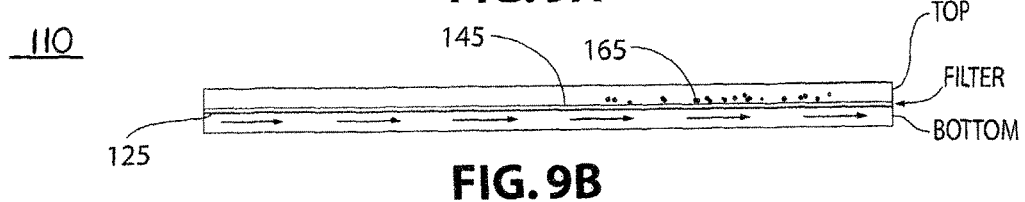

Directing attention to FIGS. 9A and 9B, valves C, E, G, and H are closed and water is introduced into the water channel 172 through the water inlet 170 and then into the second-stage channel 190 along arrows 194. With suction provided in the bottom channel 150, any undersized particles and the elution fluid remains are again drawn through the filter 125 into the bottom channel 150 where they follow the flow of arrows 196 and are discharged through the suction outlet 140.

Figure 10A:
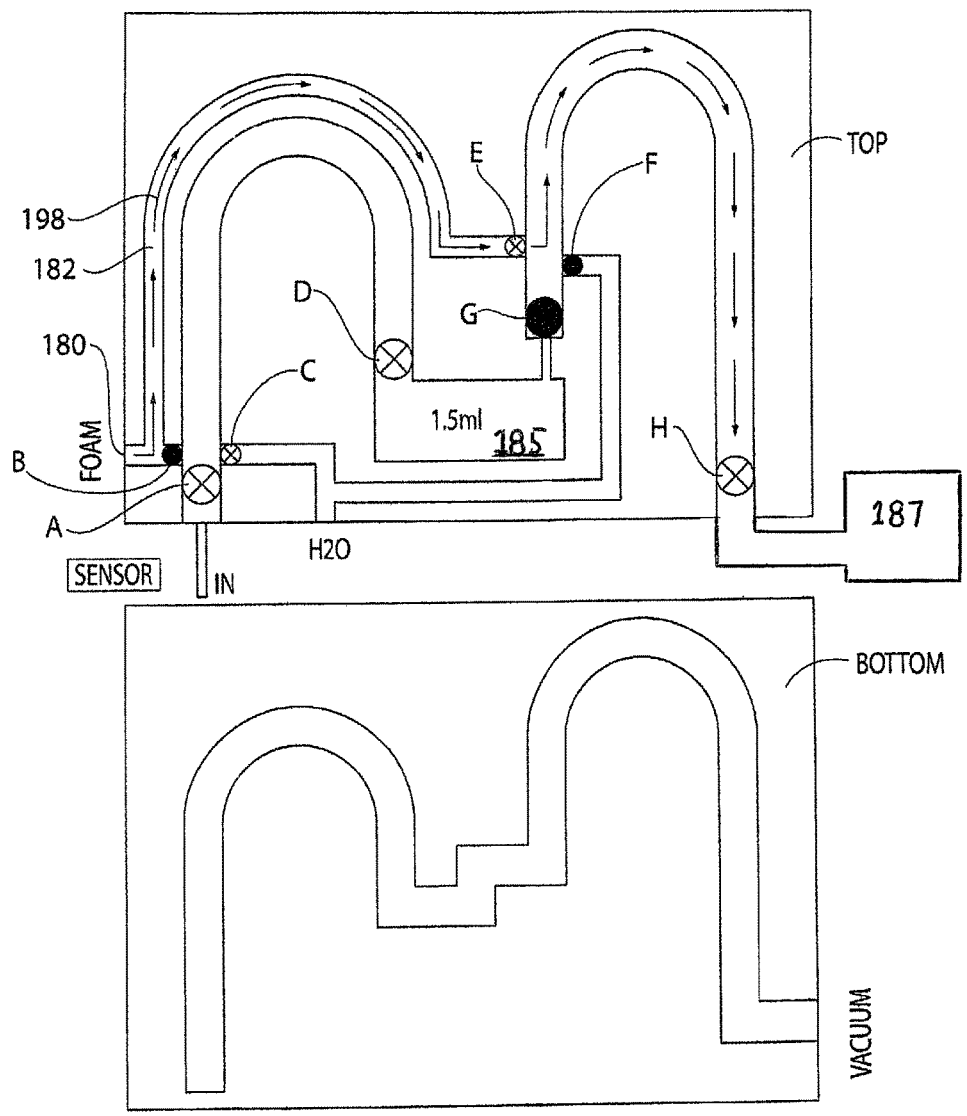
Figure 10B:
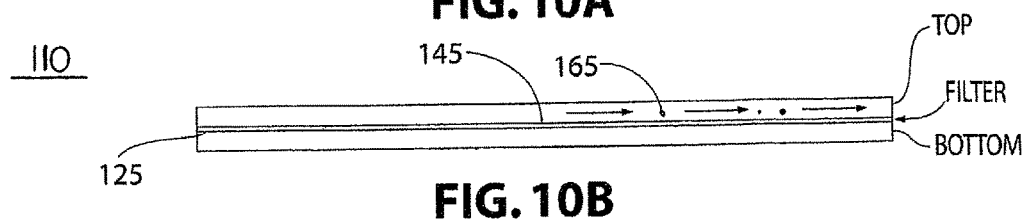

Finally, directing attention to FIGS. 10A and 10B, valves B, G, and F are closed and elution fluid is provided by the foam inlet 180 along the foam channel 182, as indicated by arrows 198. Just as before, the elution fluid moves transversely across the upper surface 145 of the filter element 125 and scrapes the particles 165 from the upper surface 145 of the filter element 125, where they are then transported through the outlet 135 into a second collector to provide a fluid/particle mixture, wherein the fluid has an exceptionally low fluid volume relative to the particle concentration, thereby allowing analysis of the particles to proceed with greater ease. As a result, the first stage channel is separated from the second stage channel by valves such that the first stage channel processing provides a concentrated sample in only the first collector and thereafter the concentrated sample from the first collector is processed in the second stage channel to supply the second collector.

Overall, FIGS. 5-10 illustrate the filter arrangement 110 for isolating particles 165 from a fluid/particle mixture. The filter arrangement is made of a top element 115 having at least one open channel 160 extending thereacross connecting a top element inlet 130 to a first collector 185, wherein the channel 160 is open on the underside 147 of the top element 115. A bottom element 120 having at least one open channel 150 extending thereacross connected to a bottom element outlet, or suction outlet 140. The channel 150 is open on the upper side 152 of the bottom element 120. The top element 115 is secured to the bottom element 120 such that the underside 147 of the top element 115 is secured against the upper side 152 of the bottom element 120 and wherein the channels 160, 150 align with one another. The filter element 125 is generally flat and is positioned between the top element 115 and the bottom element 120 and overlaps with the channels 160, 150.

The top element inlet 130 of the filter arrangement 110 is connected to a fluid/particle supply and top element inlets 180A and 180B to an elution fluid supply, wherein the bottom element outlet 140 is connected to a suction supply. As discussed, the filter arrangement provides a valve arrangement with at least two flow configurations.

With suction applied to the bottom element outlet 140, the fluid/particle mixture is introduced into the top channel 160 and over the filter element 125 thereby depositing retentate particles 165 upon the filter element 125 and passing permeate particles through the filter element 125. Thereafter, with suction discontinued to the bottom element outlet 140, the elution fluid is introduced into the top channel 160 and over the filter element 125 such that the retentate particles deposited upon the filter element 125 are tangentially rinsed and collected through the top element outlet 135 into a first collector 185.

A second collector 187 may be positioned within the path of the open channel 160 of the top element 115 to define a first stage channel 160 on one side of the first collector 185 and a second stage channel on the other side of the first collector 185. The valve arrangement described with respect to the first collector 185 for the first stage channel is repeated for the second stage channel thereby providing a two-stage filter arrangement with retentate initially deposited within the first collector and thereafter finally being deposited within the second collector.

Prior to introducing the elution fluid and after introducing the fluid/particle mixture, with suction applied to the bottom element outlet 140, the rinsing solution is introduced into the top channel 160 and through the filter element 125.

What has so far been described is a filter arrangement utilizing on/off valves A-H to provide different configurations of the subject filter arrangement. In an alternate embodiment, certain of the valves A-H illustrated in FIGS. 5A-10A may be replaced with check valves since there is flow in only a single direction through certain valves. By substituting check valves for these on/off valves where possible, the number of controlled elements may be reduced, thereby not only making control of the filter arrangement easier, but such check valves are less expensive than the on/off valves and, as a result, it is possible to fabricate a disposable filter arrangement that will cost less.

The reference characters associated with the elements in FIG. 11A and FIG. 11B are similar to those reference characters found in FIGS. 5A and 5B, for example, with the exception, however, that each of the valve identifiers, while utilizing the same capital letter, introduces the suffix "1" while the other elements utilize a suffix "A" or, in the event the previous element has now been made into two parts, the suffix "B" will also be used.

With respect to FIGS. 5A and 5B, FIGS. 11A and 11B include a first bottom channel 150A and a second bottom channel 150B as opposed to a single bottom channel 150 illustrated in FIG. 5A. Additionally, each bottom channel 150A, 150B includes a suction outlet 140A, 140B to direct fluid in the direction indicated by arrows 167A, 167B, respectively. Additionally, with respect to FIG. 7A, FIG. 11A includes a first foam inlet 180A and a second foam inlet 180B as opposed to a single foam inlet 180. With respect to FIG. 6A and water inlet 170, FIG. 11A includes two separate water inlets 170A, 170B. By enabling different elution/rinsing fluids within each of the two water inlets 170A, 170B and foam inlets 180A, 180B, it is possible to enable different elution and rinsing fluids in a first cycle and in a separate second cycle. This will allow buffer exchange between the first cycle and the second cycle. Additionally, through the use of separate suction outlets 140A, 140B, it is possible for the second suction outlet 140B to be used to draw the elution fluid into the second chamber.

Directing attention to FIG. 11A, while valves A1-H1 are illustrated in the top element 15A, it should be appreciated that valves A1-C1 and E1-G1 are check valves, while valves D1 and H1 are on/off valves. For those lines in which flow occurs only in a single direction, the inventor has realized that a single check valve may be substituted for an on/off valve, thereby relieving the operator of the duty of adjusting a valve for operation.

As previously discussed with respect to FIGS. 5A-9A, the filter arrangement 110 may be configured for six separate stages. These stages will hereinafter be referred to as: 1) aspirate sample; 2) first rinse; 3) first extraction; 4) second aspiration; 5) second rinse; and 6) final extraction.

For the initial configuration to aspirate the sample, the fluid/particle mixture is introduced through the inlet 130A and travels through the first stage channel 160A. Valve D1 is closed and the vacuum is activated such that the suction outlet 140A draws a vacuum through the bottom channel 150A, thereby depositing particles 165. With particles 165A deposited upon the upper surface 145A of the filter 125A, the first rinse stage begins. Water is introduced at water inlet 170A through check valve C1 and into the first stage channel 160A while the suction provided by the suction outlet 140A pulls the water/particle mixture through the filter 125A filtering additional particles that may not have been filtered during the initial step. The vacuum from the suction outlet 140A is discontinued and the on/off valve D1 is opened. At this point, elution is introduced under pressure at the foam inlet 180A where the liquid proceeds past the check valve B1 into the first stage channel 160A where it wipes the particles 165 from the top upper surface 145A of the filter element 125A into the collector 185A.

Any positive pressure that may be caused by the elution foam breaking down into a liquid may be vented through check valve G1.

At this point, the second aspiration stage begins with vacuum provided at the suction outlet 140B and valve H1 in the closed position. The particle/liquid solution is drawn from the collector 185A and past valve G1 into the second stage channel 190A where it then passes through the filter element 125A into the bottom channel 150B where the elution fluid and undersized particles are removed while the oversized particles 165A remain on the upper surface 145A of the filter element 125A.

In the second rinse stage, the suction outlet 140B is still energized but water is now introduced into the second stage channel 190A through the water inlet 170B. The water is pulled through the filter 125A and washes additional particles from the upper surface 145A of the filter element 125A through the suction outlet 140B where it is disposed.

The last stage is the final extraction, whereby there is no suction provided through the bottom channel 150B but elution fluid is introduced through foam inlet 180B where it travels into the second stage channel 190A. Valve H1 is open such that the elution fluid displaces the particles 165A from the upper surface 145A of the filter element 125A and moves them past the open valve H1 into a final receptacle (not shown). By doing this, particles are provided in a relatively low volume elution fluid which thereafter may be further analyzed with greater ease.

The embodiment just discussed in general replaced a number of on/off valves with check valves to make control of the multiple stages of the filter arrangement easier and to reduce parts.

FIGS. 12A-17A and 12B-17B illustrate yet another embodiment, whereby a series of three-way stopcock valves M, N, O, P are utilized to configure the filter arrangement for different stages. Once again, the discussion will be directed to the six stages previously discussed including: 1) aspirate sample; 2) first rinse; 3) first extraction; 4) second aspiration; 5) second rinse; and 6) final extraction.

Figures 12A, 12B:
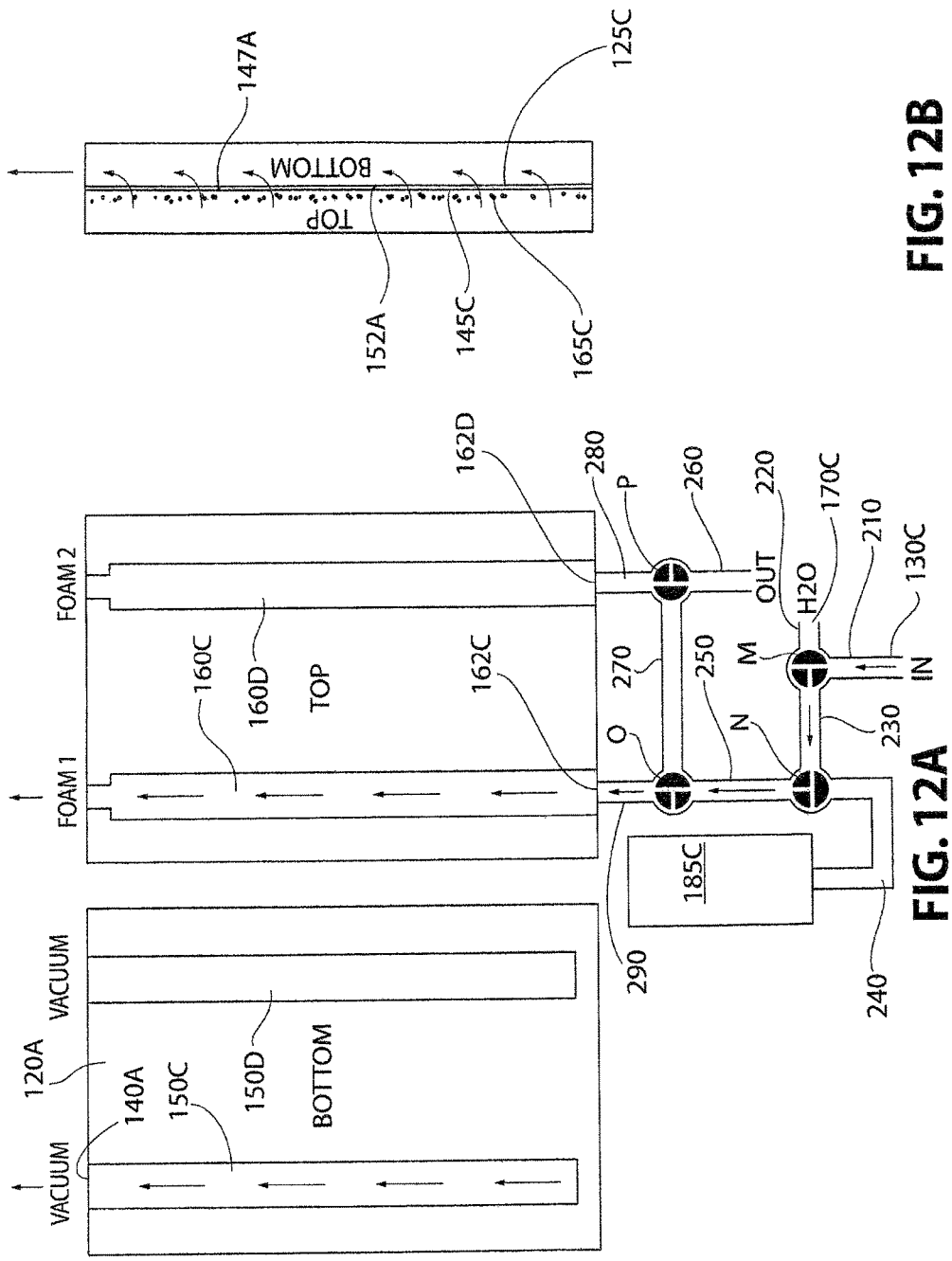
Figures 15A, 15B:
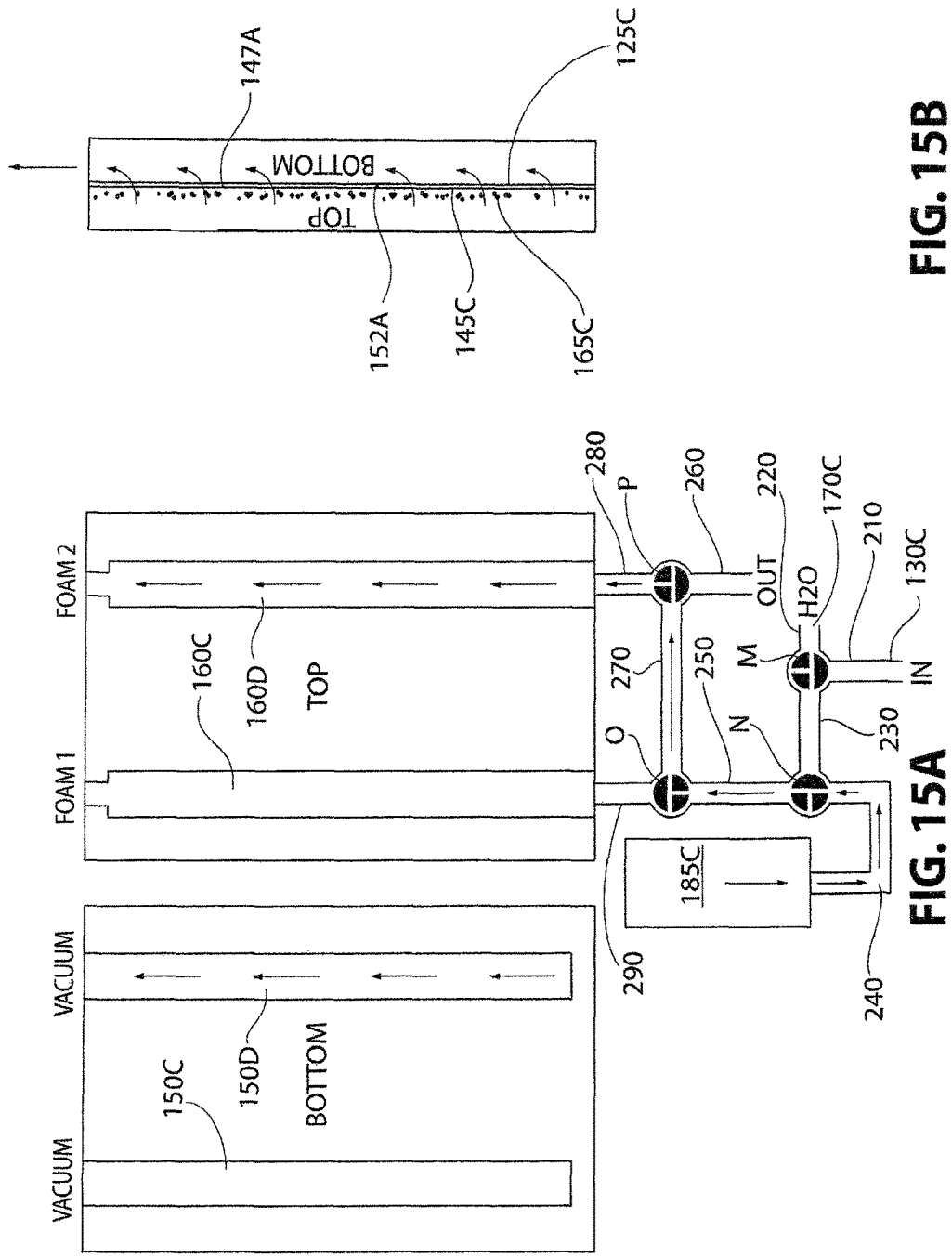

FIGS. 12A and 12B are directed to the stage of aspirating the sample, wherein the bacteria sample is introduced through inlet 130C and valves M, N, and O are oriented such that the flow is directed through passageways 210, 230, 250, and 290 and into the first stage channel 160C. Vacuum is applied to the bottom channel 150C such that particles 165C are retained on the upper surface 145C of the filter element 125C. The liquid and particles that pass through the filter element 125C are discarded.

Directing attention to FIGS. 13A and 13B, with the particles 165C retained on the upper surface 145C of the filter element 125C, water is introduced by orienting valves M, N, and O such that water enters at the top element inlet 170C and travels through passageways 220, 230, 250, and 290 into the first stage channel 160C. With a vacuum applied in bottom channel 150C, the water and undersized particles travel through the filter element 125C and are discarded, thereby providing additional filtering of undersized particles.

With particles 165C deposited upon the upper surface 145C of the filter element 125C, those particles may now be extracted. Directing attention to FIGS. 14A and 14B, elution is introduced through the first stage channel 160C and valves O and N are oriented such that the flow proceeds through passageways 290, 250, and 240 into the collector 185C. The elution moves the particles 165C across the upper surface 145C of the filter element 125C and into the passageway 290. In this manner, a relatively low volume of elution is mixed with the particles 165C and deposited within the collector 185C.

Any positive pressure that may be caused by the elution foam breaking down into a liquid may be vented through the top of the collector, which is open.

The elution/particle mixture now deposited in the collector 185C may be processed through a second filtering procedure which includes a second stage of aspirating. Directing attention to FIGS. 15A and 15B, valves N, O, and P are oriented such that the elution/particle mixture in the collector 185C through a vacuum applied to the bottom channel 150D, is moved through passageways 240, 250, 270, and 280 into the second stage channel 160D and, once again, particles 165C are deposited on the upper surface 145C of the filter element 125C.

Figure 16B:
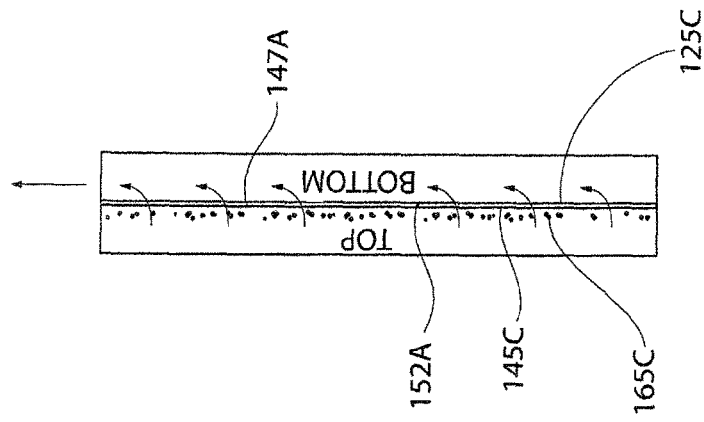
Figure 16A:
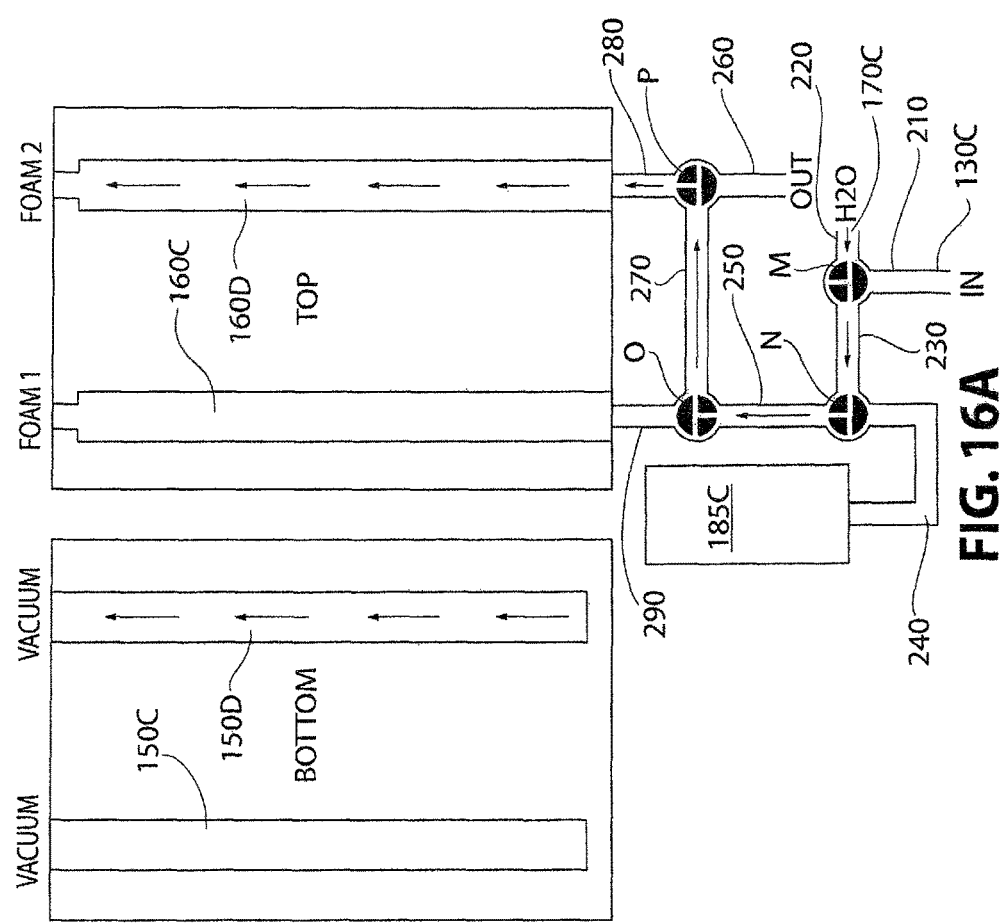

The second rinse stage, illustrated in FIGS. 16A and 16B, may now be initiated. In particular, with valves M, N, O, and P oriented as illustrated, water may be introduced at the water inlet 170C such that it travels through passageways 220, 230, 250, 270, and 280 and into the second stage channel 160D. There the water and smaller particles pass through the filter element 125C and are discarded to provide a better sampling of particles 165C.

Figures 17A, 17B:
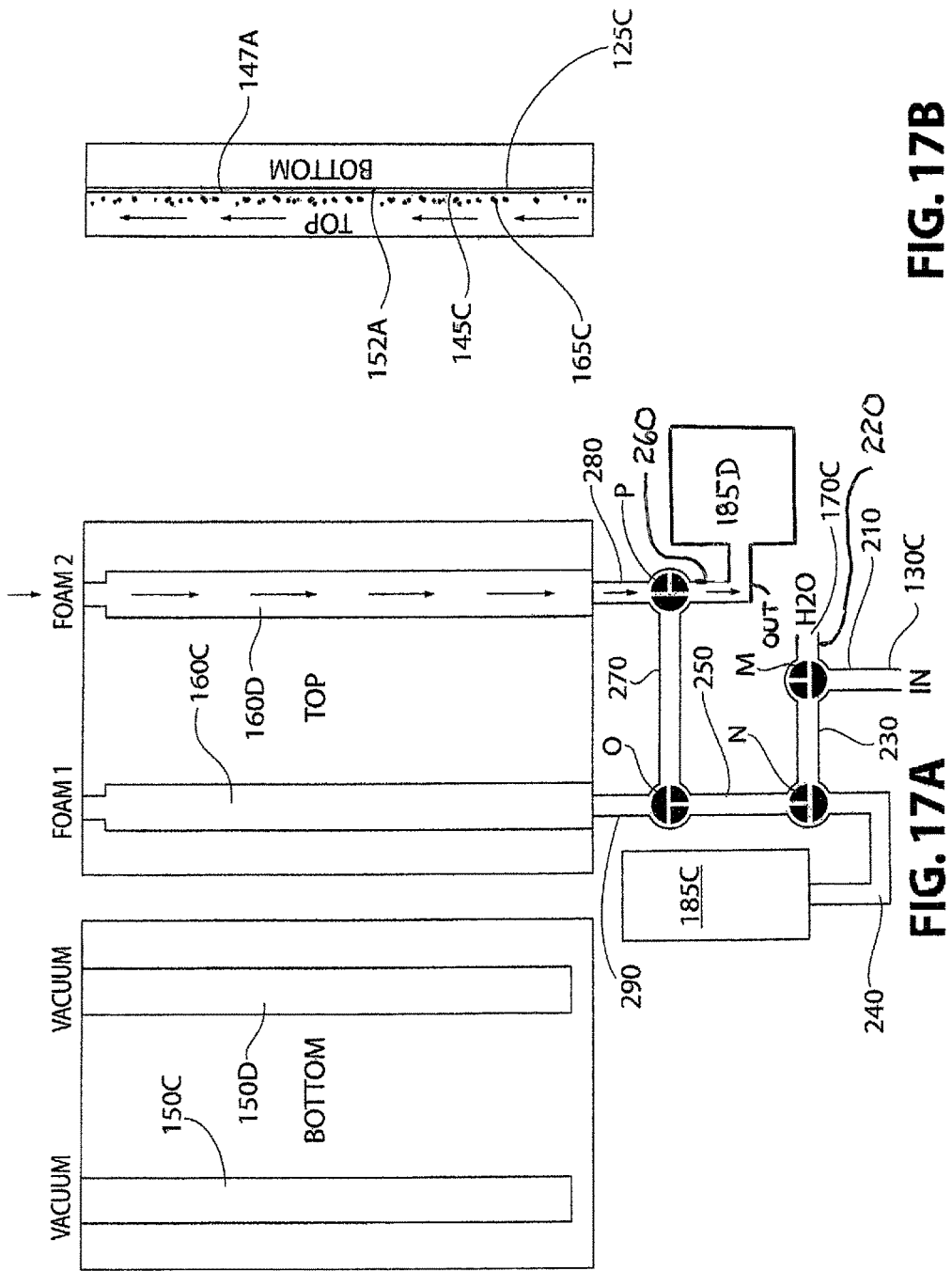

Now the second stage may be completed with a final extract as indicated in FIGS. 17A and 17B. In particular, with the particles 165C deposited upon the upper surface 145C of the filter element 125C, elution under pressure is introduced into the second stage channel 160D, thereby displacing the particles 165C from the upper surface 145C. With valve P oriented as shown, the particles and the elution are washed through the second stage channel 160D into passageway 280 through valve P where they travel through passageway 260 into a final collector 185D, providing a high quality sample of particles 165C mixed within a relatively low volume of liquid.

FIGS. 12A-17A and 12B-17B illustrate a filter arrangement having two separate channels 160C, 160D each capable of accepting an independent supply of elution and, furthermore, a series of valves M, N, O, and P permit the original particle liquid sample to be directed to either the first stage channel 160C or the second stage channel 160D. Furthermore, this configuration permits water through inlet 170C to be introduced into either the first stage channel 160C or the second stage channel 160D.

Overall, FIGS. 12A-17A and 12B-17B illustrate an alternate filter arrangement for isolating particles 165 from a fluid/particle mixture. The filter arrangement is made of a top element having at least one open 160C channel extending thereacross in fluid communication with a top channel inlet/outlet 162C to a first collector 185C wherein the channel 160C is open on the underside 147A of the top element 115. A bottom element 120A having at least one open channel 150C extending thereacross connected to a bottom element outlet, or suction outlet, 140A. The channel 150C is open on the upper side 152A of the bottom element 120A. The top element 115A is secured to the bottom element 120A such that the underside 147A of the top element 115A is secured against the upper side 152A of the bottom element 120A and wherein the channels 160C, 150C align with one another. The filter element 125A is generally flat and is positioned between the top element 115A and the bottom element 120A and overlaps with the channels 160C, 150C.

The top channel inlet/outlet 162C of channel 160C of the filter arrangement is connected to a fluid/particle supply and an elution fluid supply, wherein the bottom element outlet 140A is connected to a suction supply. As discussed, the filter arrangement provides a valve arrangement with at least two flow configurations.

With suction applied to the bottom element outlet 140A, the fluid/particle mixture is introduced through the top channel inlet/outlet 162C into the top channel 160C and over the filter element 125C thereby depositing retentate particles 165A upon the filter element 125C and passing permeate particles through the filter element 125C. Thereafter, with suction discontinued on the bottom element outlet 140A, the elution fluid is introduced into the top channel 160C and over the filter element 125C such that the retentate particles deposited upon the filter element 125C are tangentially rinsed through the top channel inlet/outlet 162C and collected into collector 185C.

The top element 115A may have a second stage channel 160D extending thereacross in fluid communication with another top channel inlet/outlet 162D to define a first stage channel 160C on one side of the top element 115A and a second stage channel 160D on the other side of the top element 115A such that the valve arrangement described in parts 1) and 2) for the first stage channel 160C is repeated for the second stage channel 160D thereby providing a two-stage filter arrangement with retentate initially deposited within the collector 185C and thereafter being processed again and finally being redeposited within the collector 185C.

The top element inlet 170C may be connected to a rinsing solution supply. Under these circumstances, the valve arrangement may have an additional configuration.

In particular, prior to introducing the elution fluid and after introducing the fluid/particle mixture, with suction applied to the bottom element outlet 135 outlet 140A, the rinsing solution is introduced into the top channel 160D at the top channel inlet/outlet 162D and through the filter element 125C.

Just as before and as described with respect to the first stage channel 160C, the second stage channel 160D may have a similar valve configuration such that the processing of fluid retained in the collector 185C from the first stage channel 160C may be introduced into the second stage channel 160D for further processing and refinement, after which the refined particles are redeposited within the collector 185C.

While predefined steps utilizing this filter arrangement have been described herein, it should be appreciated that depending upon the specific need, there may be a single stage utilized or multiple stages and the individual steps or the sequence of steps may be different.

Figure 18A:
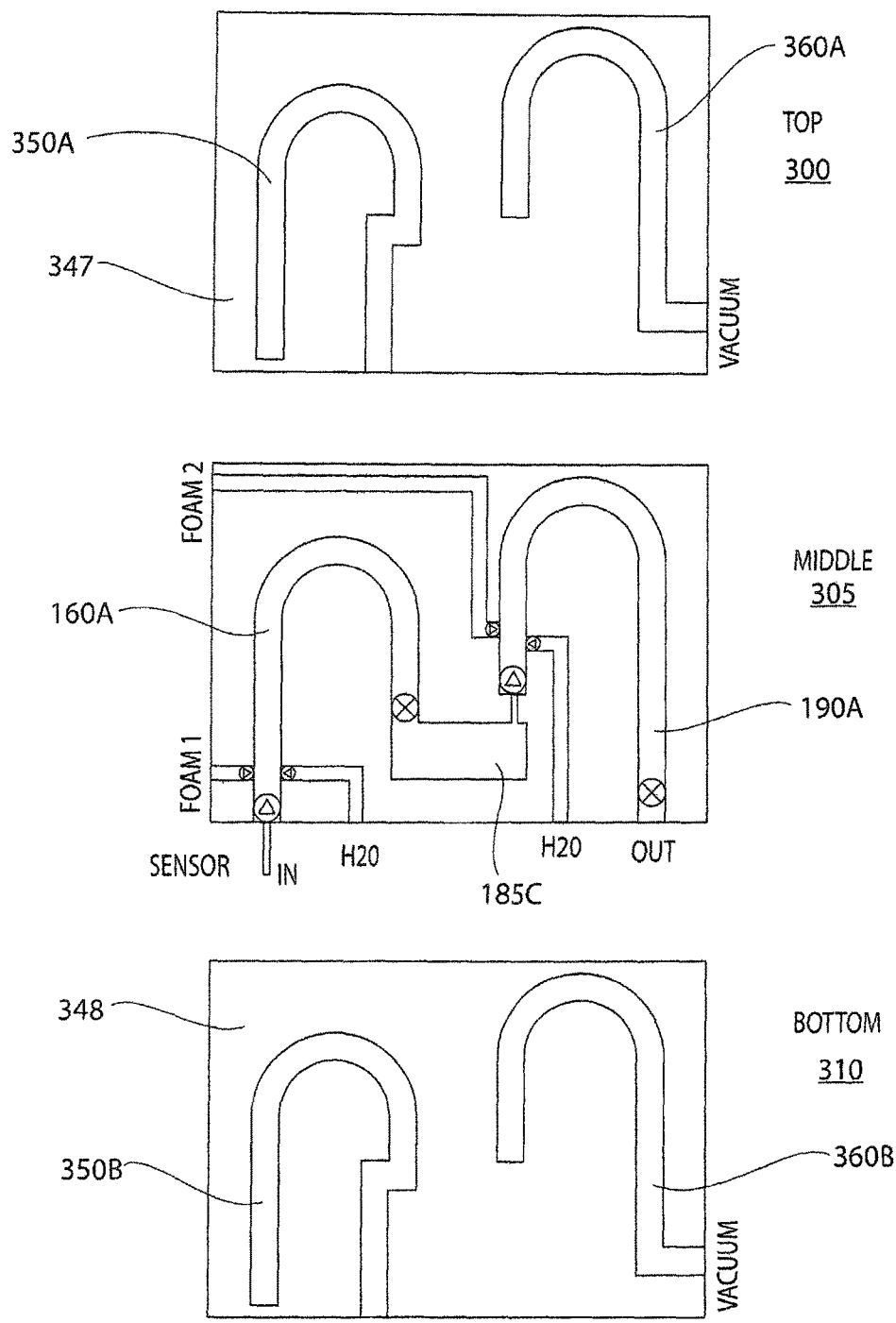
FIG. 18A is a schematic view of a filter arrangement utilizing a sandwiching arrangement, whereby a previously described "top portion" is sandwiched between two "bottom portions" to provide greater filtering capacity.
Figure 18B:
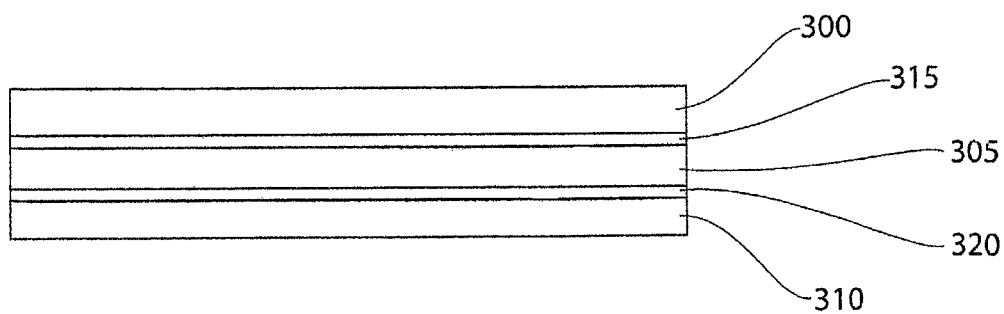
FIG. 18B is a schematic view of the filter arrangement in FIG. 18A in the assembled state.

In a further embodiment, a dual filtering arrangement is possible as illustrated in FIGS. 18A and 18B. In particular, FIG. 18A illustrates a top sandwich element 300 identical to the bottom element 120A illustrated in FIG. 11A and illustrates a middle sandwich element 305 similar to the top element 115A illustrated in 11A. However, the channels 160A, 190A of the middle sandwich element 305 extend completely through the thickness of the middle sandwich element 305. The channels 160A, 190A are in fluid communication with a collector 185C. Furthermore, a bottom sandwich element 310 is identical to the top sandwich element 300. However, the channels 350A, 360A are on the underside 347 of the top sandwich element 300 while the channels 350B, 360B are on the upper side of the bottom sandwich element 310.

As previously discussed, it should be appreciated that the view of the top sandwich element 300 is a transparent view and, in actuality, the channels are on the underside of the top sandwich element 300. Additionally, the channels in the bottom sandwich element 310 are on the upper side of the bottom sandwich element 310 such that, directing attention to FIG. 18B, when the top sandwich element 300, the middle sandwich element 305, and the bottom sandwich element 310 are placed together, the channels are aligned with one another. Placed between the top sandwich element 300 and the middle sandwich element 305 is a top filter element 315 and placed between the middle sandwich element 305 and the bottom sandwich element 310 is a bottom filter element 320. By utilizing this configuration, the top filter element 315 and the bottom filter element 320 provide twice the membrane surface with the same channel volume.

Any positive pressure that may be caused by the elution foam breaking down into liquid may be vented through the check valve immediately downstream of the collector 185C.

Additionally, the filter elements discussed herein may be made up of a hydrophobic membrane to allow the passage of trapped air to the vacuum side.

Finally, a flow sensor may be added to the vacuum side to sense when all of the sample has been aspirated, thereby alleviating the need to have a sensor on the "clean side" of the disposable filter.

The method disclosed herein provides for the use of wet foam to remove microorganisms from a membrane surface and resuspend them in a fluid of choice. It is also possible to provide high recovery for low concentration specimens while maintaining consistency regardless of the specimen source.

The filter element provides 0.4 micron filtration of permeate and removes proteins, soluble materials and cell fractions. Additionally, by rinsing the filter element with rinsing solution, it is possible to remove small surface hanging particles and droplets from the original matrix while the use of wet foam allows extraction of the microorganisms from the surface of the filter.

It should be noted that the filter arrangement illustrated herein, for example in FIGS. 5A-11B, FIGS. 12A-17B and FIGS. 18A-18B, are all made up of a single cassette as shown from the "B" figures of these sets.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the appended claims and any and all equivalents thereof.

The invention claimed is:

1. A filter arrangement for isolating particles from a fluid/particle mixture comprised of a single cassette having:
   a) a top element having at least one open channel extending thereacross connecting a top element inlet to a first collector and to a second collector, wherein the channel is open on an underside of the top element and wherein the top element is connected to a fluid/particle supply and an elution fluid supply, wherein the elution fluid is intended to tangentially rinse particles from the top element;

b) a bottom element having at least one open channel extending thereacross connected to a bottom element outlet which is connected to a suction supply for providing suction, wherein the channel is open on an upper side of the bottom element;

c) wherein the top element is secured to the bottom element such that the underside of the top element is secured against the upper side of the bottom element and wherein the channels align with one another;

d) a filter element which is generally flat and has an upper surface and an opposing lower surface, and wherein the filter is positioned between the top element and the bottom element and overlapping with the channels, such that the upper surface of the filter is contiguous with the underside of the top element and the lower surface of the filter is contiguous with the upper side of the bottom element;

e) wherein the top element open channel and the bottom element open channel extend beyond the first collector from a top element outlet into a second collector to define a first stage channel on one side of the first collector and a second stage channel on the other side of the first collector; and f) wherein the first stage channel is separated from the second stage channel by valves such that first stage channel processing provides a concentrated sample in only the first collector and thereafter the concentrated sample from the first collector is processed in the second stage channel to supply the second collector.

2. A method of using the filter arrangement according to claim 1 comprising the steps of:

a) with suction applied to the bottom element outlet, introducing the fluid/particle mixture into the first stage channel of the top channel and over the filter element thereby depositing retentate particles upon one portion of the filter element and passing permeate particles through the filter;

b) thereafter, with suction discontinued to the bottom element outlet, introducing elution fluid into the top channel and over the filter element such that the retentate particles deposited upon the filter are tangentially rinsed and collected into the first collector; and c) after step b), with suction applied to the bottom element outlet, introducing the retentate into the second stage channel of the top channel and over the filter element thereby depositing retentate particles upon another portion of the filter element and passing permeate particles through the filter; and d) thereafter with suction discontinued to the bottom element outlet, introducing the elution fluid into the top channel and over the filter element such that the retentate particles deposited upon the filter are tangentially rinsed and collected into the second collector, thereby providing a two-stage filter arrangement with retentate initially deposited within the first collector and thereafter finally being deposited within the second collector.

3. The method according to claim 2, further comprising the step, immediately after each step a) and c), of applying suction to the bottom element outlet and introducing rinsing solution into the top channel and through the filter element to rinse the retentate.

4. The filter arrangement according to claim 1, wherein the filter arrangement further comprises:

f) a valve arrangement comprising:
1) a first position wherein with suction applied to the bottom element outlet, introducing the fluid/particle mixture into the top channel and over the filter element on a first side of the first collector thereby depositing retentate particles upon the filter element and passing permeate particles through the filter on the first side of the first collector;
2) a second position wherein with the suction discontinued to the bottom element, introducing the elution fluid into the top channel and over the filter element such that the retentate particles deposited upon the filter are tangentially rinsed and collected into the first collector.

5. The filter arrangement according to claim 4, wherein the filter arrangement further comprises:

g) a valve arrangement wherein the top element inlet is further connected to a rinsing solution supply and wherein the valve arrangement comprises:
1) a third position wherein prior to introducing the elution fluid and after introducing the fluid/particle mixture, with the bottom element outlet suction applied, introducing the rinsing solution from the rinsing solution supply into the top channel of the first stage channel and through the filter element.

6. The filter arrangement according to claim 1, wherein the filter arrangement further comprises:

g) a valve arrangement comprising:
1) a first position wherein with suction applied to the bottom element outlet, introducing the fluid/particle mixture into the top channel and over the filter element on a second side of the first collector thereby depositing retentate particles upon the filter element and passing permeate particles through the filter on the second side of the first collector;
2) a second position wherein with the suction discontinued to the bottom element, introducing the elution fluid into the top channel and over the filter element such that the retentate particles deposited upon the filter are tangentially rinsed and collected into the second collector.

7. The filter arrangement according to claim 6, wherein the filter arrangement further comprises:

h) a valve arrangement wherein the top element inlet is further connected to a rinsing solution supply and wherein the valve arrangement comprises:
1) a third position wherein prior to introducing the elution fluid and after introducing the fluid/particle mixture, with the bottom element outlet suction applied, introducing the rinsing solution from the rinsing solution supply into the top channel of the second stage channel and through the filter element.

8. The filter arrangement according to claim 1, wherein the filter element is made of a membrane and the membrane of the filter element associated with the first stage channel and the second stage channel is identical.

9. Using a fluid/particle mixture and a filter element that captures over-sized particles and allows undersized particles to pass through, a method for separating the particles from a fluid/particle mixture with a filter arrangement for isolating particles from a fluid/particle mixture using a single cassette comprising the steps of:

a) providing a top element having at least one open channel extending thereacross connecting a top element inlet to a first collector, wherein the channel is open on an underside of the top element and wherein the top element is connected to a fluid/particle supply and an elution fluid supply;

b) providing a bottom element having at least one open channel extending thereacross connected to a bottom element outlet which is connected to a suction supply for providing suction, wherein the channel is open on an upper side of the bottom element;

c) securing the top element to the bottom element such that the underside of the top element is secured against the upper side of the bottom element and wherein the channels align with one another;

d) providing a filter element which is generally flat and has an upper surface and an opposing lower surface, and wherein the filter is positioned between the top element and the bottom element and overlapping with the channels, such that the upper surface of the filter is contiguous with the underside of the top element and the lower surface of the filter is contiguous with the upper side of the bottom element; wherein the top element open channel and the bottom element open channel extend beyond the first collector from a top element outlet into a second collector to define a first stage channel on one side of the first collector and a second stage channel on the other side of the first collector;

e) filtering the fluid/particle mixture through the filter element on each of a side of the first collector so that the oversized particles are deposited on an upper surface of the filter element;

f) tangentially rinsing the upper surface of the filter element with an elution fluid to displace the entrapped particles;

g) collecting the displaced particles and the elution fluid; and h) repeating steps e) through g) to provide a second stage of filtering; wherein the first stage channel is separated from the second stage channel by valves such that the first stage channel processing provides a concentrated sample in only the first collector and thereafter the concentrated sample from the first collector is processed in the second stage channel to supply the second collector.

10. The method for separating particles according to claim 9, wherein the filter element is made of a membrane and the membrane of the filter element associated with the first stage channel and the second stage channel is identical.

* * * * *